(12) United States Patent
Kin et al.

(10) Patent No.: US 7,318,910 B2
(45) Date of Patent: Jan. 15, 2008

(54) CHEMICAL DOSIMETER

(75) Inventors: Pong Boon Kin, Singapore (SG); Ang Kiam Wee, Singapore (SG)

(73) Assignee: DSO National Laboratories, Singapore (SG)

( * ) Notice: Subject to any disclaimer, the term of this patent is extended or adjusted under 35 U.S.C. 154(b) by 470 days.

(21) Appl. No.: 10/209,755

(22) Filed: Jul. 31, 2002

(65) Prior Publication Data
US 2003/0215958 A1 Nov. 20, 2003

(30) Foreign Application Priority Data
May 20, 2002 (SG) ............................... 200203010

(51) Int. Cl.
*G01N 30/96* (2006.01)

(52) U.S. Cl. .......................... 422/88; 422/83; 436/178; 73/29.02; 96/151

(58) Field of Classification Search .................. 422/56, 422/58, 61, 83, 88; 436/174–178; 96/108, 96/151, 153; 73/29.02, 31.07
See application file for complete search history.

(56) References Cited

U.S. PATENT DOCUMENTS

| | | | | |
|---|---|---|---|---|
| 3,972,225 A | * | 8/1976 | Fort et al. | 73/28.04 |
| 4,833,083 A | * | 5/1989 | Saxena | 435/403 |
| 5,482,677 A | * | 1/1996 | Yao et al. | 422/88 |

\* cited by examiner

*Primary Examiner*—Lyle A. Alexander
(74) *Attorney, Agent, or Firm*—Hancock Hughey LLP

(57) ABSTRACT

A chemical dosimeter comprising: a chamber defined by a heat resistant mesh; and a quantity of an adsorbent contained within the chamber; the arrangement being such that gas may diffuse into the chamber through the heat resistant mesh so that chemicals in the gas may be adsorbed by the adsorbent.

21 Claims, 1 Drawing Sheet

CHEMICAL DOSIMETER

In many modem environments, toxic chemical vapours can pose significant health hazards. Such vapours may be present in public areas, as well as in places of work.

Where it is expected, or possible, that workers will be exposed to hazardous chemicals, the workers are generally equipped with protective garments. However, these protective garments are subject to wear and tear, and ultimately become ineffective barriers to the toxic chemicals against which they are designed to protect.

Analysis of protective garments prior to use to determine the effectiveness thereof is generally not possible, since these tests are typically destructive and would significantly lower the effectiveness of the garment.

In view of the above, it is desirable to equip workers who routinely wear protective garments with a chemical dosimeter, which is located beneath a protective garment, to provide and indication of toxic chemicals that have penetrated the garment, and hence may pose a hazard to the occupant thereof.

Monitoring of chemical vapours may also be desirable in buildings and homes. The so-called "sick building syndrome" is becoming increasingly more common, as chemical coatings are used widely on walls, furniture, floors and so forth, and these coatings may release small amounts of potentially harmful substances over long periods of time. While the presence of these substances in the air is usually in concentrations too small to be detected by the human olfactory sense, the exposure to these substances over long periods of time is believed to be the cause of many health complaints.

Methods of monitoring airborne chemical vapours include the bubbling of a known quantity of air through an absorbing solution and measuring the concentrations of impurities within the solution, and the passing of a known quantity of gas through a column of absorbent, and subsequently analysing the absorbent column. However, devices implementing these methods are generally bulky, and unsuitable to be worn under a protective garment.

A further drawback of many such systems is that a colourimetric system for analysis is employed, colourimetric systems generally do not provide the sensitivity required to detect the small amounts of a chemical vapour that may penetrate through a protective garment.

It is an object of the present invention to seek to provide a chemical dosimeter that alleviates some or all of the above problems.

Accordingly, one aspect of the present invention provides a chemical dosimeter comprising: a chamber defined by a heat resistant mesh; and a quantity of an adsorbent contained within the chamber; the arrangement being such that gas may diffuse into the chamber through the heat resistant mesh so that chemicals in the gas may be adsorbed by the adsorbent.

Advantageously, the chamber is open-ended.

Preferably, a plug is located at the open end of the chamber.

Conveniently, the plug is porous.

Advantageously, the plug is formed from glass wool or steel wool.

Preferably, the chamber is in the form of a tube having two open ends, the tube being formed from a rolled sheet of the heat resistant mesh.

Conveniently, the adsorbent is in the form of a powder.

Advantageously, the interstices in the heat resistant mesh are sufficiently small to prevent egress of the adsorbent powder from the chamber through the interstices.

Preferably, the heat resistant mesh is capable of withstanding temperatures in excess of about 250° C.

Conveniently, the heat resistant mesh is formed from stainless steel.

Advantageously, the dosimeter has more than one adsorbent contained within the chamber.

Preferably, the respective adsorbents are operable to adsorb different chemicals.

Conveniently, the dosimeter is operable to be analysed directly by an analyser to establish the quantity of a chemical that has been adsorbed onto the adsorbent.

Advantageously, the dosimeter is operable to be analysed directly by a Perkin-Elmer® Automated Desorption Unit.

Preferably, the entire dosimeter is heat-resistant.

Another aspect of the present invention provide a method of providing an indication of the quantity of a chemical in a gas, the method comprising the steps of: providing a chamber defined by a heat resistant mesh; placing a quantity of an adsorbent within the chamber; placing the chamber in a region of the gas, so that the gas diffuses into the chamber through the heat resistant mesh; and analysing the adsorbent to determine the quantity of the chemical that has been adsorbed onto the adsorbent.

Conveniently, the step of providing a chamber comprises the step of providing an open-ended chamber.

Advantageously, the method further comprises the step of locating a plug at the open end of the chamber.

Preferably, the step of locating a plug at the open end of the chamber comprises the step of locating a porous plug at the open end of the chamber.

Conveniently, the step of locating a plug at the open end of the chamber comprises the step of locating a plug formed from glass wool or steel wool at the open end of the chamber.

Advantageously, the step of providing an open-ended chamber comprises the step of providing a chamber in the form of a tube having two open ends, the tube being formed from a rolled sheet of the heat resistant mesh.

Preferably, the step of placing a quantity of an adsorbent within the chamber comprises the step of placing an adsorbent in the form of a powder within the chamber.

Conveniently, the step of providing a chamber defined by a heat resistant mesh comprises the step of providing a chamber defined by mesh having interstices therein which are sufficiently small to prevent egress of the adsorbent powder from the chamber through the interstices.

Advantageously, the step of providing a chamber defined by a heat resistant mesh comprises the step of providing a chamber defined by mesh which is capable of withstanding temperatures in excess of about 250° C.

Preferably, the step of providing a chamber defined by a heat resistant mesh comprises the step of providing a chamber defined by mesh which is formed from stainless steel.

Conveniently, the method further comprises the step of placing more than one adsorbent within the chamber.

Advantageously, the step of placing more than one adsorbent within the chamber comprises the step of placing adsorbents which are respectively operable to adsorb different chemicals within the chamber.

Preferably, the method further comprises the step of analysing the adsorbent directly by an analyser to establish the quantity of a chemical that has been adsorbed onto the adsorbent.

Conveniently, the step of analysing the adsorbent directly by an analyser comprises the step of analysing the chamber and the adsorbent directly using a Perkin-Elmer® Automated Desorption Unit.

In order that the present invention may be more readily understood, embodiments thereof will now be described, by way of example, with reference to the accompanying Figures, in which:

BRIEF DESCRIPTION OF THE DRAWINGS

Turning to FIG. 1, a dosimeter 1 embodying the present invention comprises a tubular chamber 2. The tubular chamber 2 is preferably formed from a rolled-up rectangular sheet.

Figure 1:
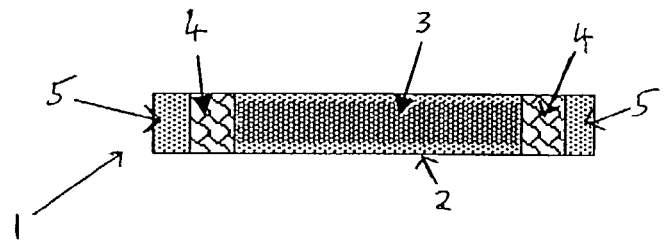
FIG. 1 is a schematic representation of a dosimeter embodying the present invention.

The tubular chamber 2 is formed from a heat-resistant mesh. Preferably, the heat-resistant mesh is capable of withstanding temperatures in excess of about 250° C. without burning, melting or otherwise being destroyed.

In preferred embodiments of the present invention, the heat-resistant mesh is formed from stainless steel. However, a skilled person will readily appreciate that many other materials would be suitable for the purpose.

A quantity of an adsorbent material 3 is provided within the tubular chamber 2. Preferably, the adsorbent material 3 is provided in the form of a powder, and in this embodiment the interstices in the heat-resistant mesh are preferably sufficiently small to prevent egress of the powder grains therethrough.

The nature of the adsorbent material 3 will depend upon the chemical vapours that it is intended to detect. Clearly, if the dosimeter 1 is adapted to detect a particular chemical vapour, then an adsorbent 3 which is highly efficient at adsorbing this vapour will be selected. Alternatively, if the dosimeter 1 is for general use, then an adsorbent material 3 which is effective at adsorbing many different types of vapour will be selected.

In preferred embodiments of the invention, more than one type of adsorbent material 3 may be provided within the tubular chamber 2, and preferably the respective adsorbent materials 3 are particularly suited to the adsorption of different chemical vapours.

Examples of adsorbent materials that may be employed with the present invention include those sold under the trademark TENAX-TA and activated carbon.

It is possible to vary and control the sensitivity of the dosimeter 1, by controlling the amount of adsorbent material 3 that is provided within the tubular chamber 2.

Once the adsorbent material 3 has been placed in the tubular chamber 2, plugs 4 are placed in the respective open ends 5 thereof. Preferably, the plugs 4 are porous, and the plugs 4 may be formed, for example, from glass wool or steel wool.

In use of the dosimeter 1, the dosimeter 1 may be worn by a person, for instance beneath a protective garment. The interstices in the heat-resistant mesh, as well as the porous nature of the plugs 4, allow gas surrounding the dosimeter 1 to diffuse into the tubular chamber 2, where chemical vapours in the gas may be adsorbed onto the adsorbent material 3 within the dosimeter 1. The dosimeter 1 is passive, and requires no power supply.

After exposure of the dosimeter 1 to gas which may contain toxic chemical vapours, the adsorbent material 3 within the dosimeter 1 is analysed.

Conveniently, the dosimeter 1 is of appropriate dimensions to be analysed directly by a Perkin-Elmer Automated Thermal Desorption Unit. Such a unit is a widely-available analysing device, and in this embodiment the length of the dosimeter 1 is around 90 mm. However, the Perkin-Elmer unit is one of several available analysing devices, and the dosimeter 1 of the present invention may be adapted to be analysed by any of those available devices.

Many conventional dosimeters employ skin-simulating permeable membranes located between the atmosphere and a quantity of adsorbent material, which membranes are adapted to simulate the permeability of human skin. While the use of such membranes has advantages with regard to estimating the quantity of a toxic vapour that may have been adsorbed through a person's skin, the use of such a permeable membrane lowers the sensitivity of the dosimeter, making the dosimeter insensitive to very low levels of chemical vapours.

In contrast, the dosimeter 1 of the present invention employs a mesh as a barrier between the adsorbent material and the outside atmosphere, and clearly the relatively large interstices in a mesh will provide substantially no hindrance to the free passage of gas between the interior of the dosimeter 1 and the outside atmosphere.

A further drawback of conventional dosimeters, when analysed by gas chromatography, is that the dosimeters may become contaminated with unknown chemicals that make it difficult to establish which substances have been collected by the dosimeter during use thereof. This difficulty cannot be overcome by cleaning the dosimeter prior to use thereof due to the typically low tolerance of permeable membranes to high temperature.

By contrast, the use of a heat-resistant mesh in the dosimeter 1 present invention allows the cleaning of the dosimeter 1 by exposure thereof to high temperatures to remove all or substantially all contaminants that may be present on the dosimeter 1 prior to use thereof. Advantageously, all of the components of the dosimeter 1, and not only the mesh, are heat resistant.

Many conventional dosimeters are also incapable of being analysed directly by conventional absorption units (for instance the Perkin-Elmer unit mentioned above). Instead, the adsorbent material has to be transferred from the dosimeter to another appropriate medium for analysis. Adsorbent materials are typically provided in the form of fine powders, which are difficult to handle, and quantities of powder may be lost during transfer. In addition, desorption of chemicals from the adsorbent material during the transfer process can lead to insensitivity in the detection process as a whole.

In contrast, in preferred embodiments of the present invention, the dosimeter 1 may be analysed directly by a Perkin-Elmer Automated Thermal Desorption Unit, and clearly such an arrangement is advantageous.

Figure 2:
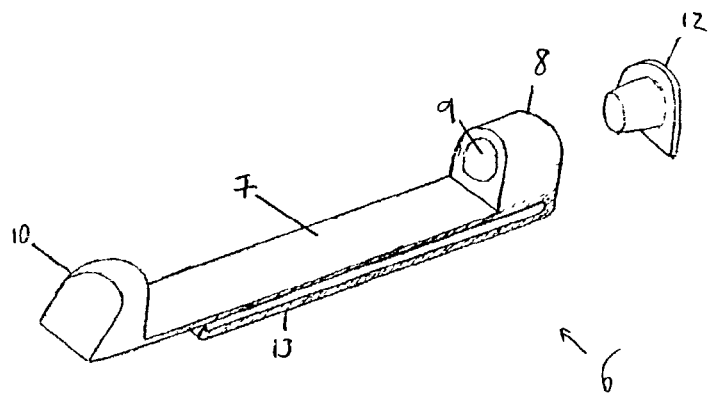
FIG. 2 is a perspective view of a dosimeter holder suitable for holding the dosimeter of FIG. 1.
Figure 3:
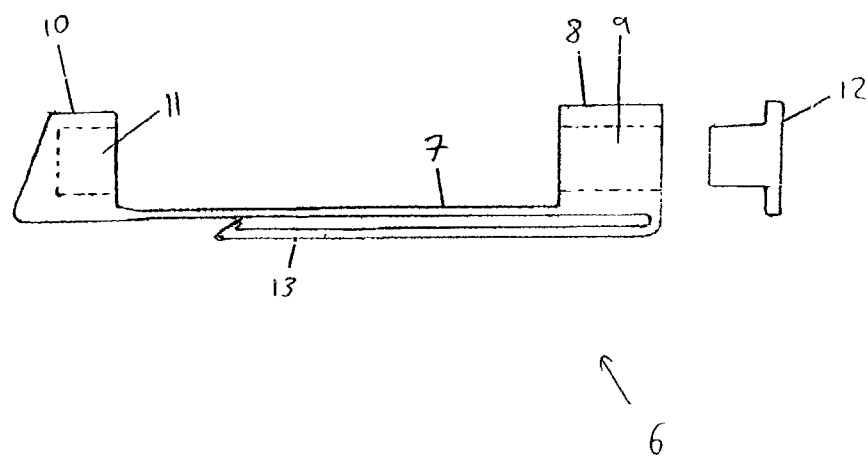
FIG. 3 is a side view of the dosimeter holder of FIG. 2.

In practical Applications of the present invention, the dosimeter 1 may be used with a dosimeter holder, for example the dosimeter holder 6 shown in FIGS. 2 and 3. The dosimeter holder 6 comprises an elongate, rigid rectangular body 7, at one end of which a first protrusion 8 having a circular bore 9 therethrough is provided. The diameter of the circular bore 9 is equal to, or slightly greater than, the diameter of the dosimeter 1. At the other end of the body 7 of the dosimeter 6, a second protrusion 10 is provided, a circular pit 11 being provided in a face of the second protrusion 10 that faces towards the first protrusion 9. The axes of the circular bore 9 and the circular pit 11 are aligned with one another.

The dosimeter holder 6 is arranged so that the dosimeter 1 may be inserted into the circular bore 9 in the first protrusion 8, and slid therethrough until the leading end of the dosimeter 1 comes to rest in the circular pit 11. Hence the dosimeter holder 6 is adapted to receive and retain the dosimeter 1.

Once the dosimeter 1 has been inserted into the dosimeter holder 6, a cap 12 is placed into the open end of the circular bore 9, to ensure that the dosimeter 1 is held securely in place. A clip 13 is provided on a reverse side of the body 7 of the dosimeter holder 6, to allow the dosimeter holder 6 to be attached to, for example, the pocket or belt of a user. The invention is not limited to a clip, and a skilled person will appreciate that there are many ways in which the dosimeter holder 6 may be attached to the clothing or equipment of a user, for instance by use of an adhesive pad.

The dosimeter holder 6 holds the dosimeter 1 firmly in place without deforming the dosimeter 1, and leaves large areas of the mesh exposed, which minimises interference with the sampling efficiency of the dosimeter 1.

It will be appreciated that the present invention provides a simple yet efficient and sensitive chemical dosimeter, which will find application in many environments where toxic chemical vapours exist or are suspected to exist.

In the present specification "comprises" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A chemical sampling device comprising:
    an open-ended chamber defined by a tubular heat resistant mesh capable of withstanding temperatures in excess of 250 degrees Celsius and in direct communication with ambient gas; and
    a quantity of adsorbent in the form of a powder and contained within the chamber wherein a porous plug is located at the open end of the chamber, the plug being formed of glass wool or steel wool;
    the arrangement being such that ambient gas may diffuse into the chamber through the heat resistant mesh so that chemicals in the gas may be adsorbed by the adsorbent.

2. A sampling device according to claim 1, wherein the chamber is in the form of a tube having two open ends, the tube being a rolled sheet of the heat resistant mesh.

3. A sampling device according to claim 1, wherein the heat resistant mesh is formed from stainless steel.

4. A chemical sampling device comprising:
    an open-ended chamber defined by a tubular heat resistant mesh capable of withstanding temperatures in excess of 250 degrees Celsius; and
    a quantity of adsorbent in the form of a powder and comprising more than one type of adsorbent and contained within the chamber;
    the arrangement being such that ambient gas may diffuse directly into the chamber through the heat resistant mesh so that chemicals in the gas may be adsorbed by the adsorbent.

5. A sampling device according to claim 4, wherein the respective adsorbents are operable to adsorb different chemicals.

6. A sampling device according to claim 1, operable to be analysed directly by an analyser to establish the quantity of a chemical that has been adsorbed onto the adsorbent.

7. A chemical sampling device comprising:
    an open-ended chamber defined by a tubular heat resistant mesh capable of withstanding temperatures in excess of 250 degrees Celsius; and
    a quantity of adsorbent in the form of a powder and contained within the chamber, wherein a plug is located at the open end of the chamber;
    the arrangement being such that ambient gas may diffuse directly into the chamber through the heat resistant mesh so that chemicals in the gas may be adsorbed by the adsorbent; and
    direct analysis means for analyzing the adsorbent material without removing the material from the chamber.

8. A sampling device according to claim 7, wherein the entire sampling device is heat-resistant and wherein the direct analysis means is also for applying thermal desorption to establish the quantity of chemicals that may be adsorbed by the adsorbent.

9. A method of providing an indication of the quantity of a chemical in ambient gas, the method comprising the steps of:
    forming a heat resistant mesh capable of withstanding temperatures in excess of 250 degrees Celsius into a tubular shape that defines an open-ended chamber;
    placing a quantity of an adsorbent within the chamber;
    placing the chamber in a region of the gas, so that the gas diffuses directly into the chamber through the heat resistant mesh;
    analysing the adsorbent to determine the quantity of the chemical that has been adsorbed onto the adsorbent; and
    locating a plug at the open end of the chamber.

10. A method according to claim 9, wherein the step of locating a plug at the open end of the chamber comprises the step of locating a porous plug at the open end of the chamber.

11. A method according to claim 9, wherein the step of locating a plug at the open end of the chamber comprises the step of locating a plug formed from glass wool or steel wool at the open end of the chamber.

12. A method according to claim 9, wherein the forming step comprises rolling a sheet of the heat resistant mesh.

13. A method according to claim 9, wherein the step of placing a quantity of an adsorbent within the chamber comprises the step of placing an adsorbent in the form of a powder within the chamber.

14. A method according to claim 13, including the step of selecting the mesh to have interstices therein which are sufficiently small to prevent egress of the adsorbent powder from the chamber through the interstices.

15. A method according to claim 9, wherein the mesh is formed from stainless steel.

16. A method according to claim 9, comprising the step of placing more than one adsorbent within the chamber.

17. A method according to claim 16, wherein the step of placing more than one adsorbent within the chamber comprises the step of placing adsorbents which are respectively operable to adsorb different chemicals within the chamber.

18. A method according to claims 9, further comprising the step of analysing the adsorbent directly by an analyser to establish the quantity of a chemical that has been adsorbed onto the adsorbent.

19. A method according to claim 18, wherein the step of analysing the adsorbent directly by an analyser comprises the step of analyzing the adsorbent without removing the material from the chamber.

20. The method of claim 9 wherein the forming step includes forming the heat resistant mesh into an elongated tubular shape, and holding the device so that gas may diffuse into the chamber along the length of the mesh between the respective ends of the elongate tubular mesh.

21. The device of claim 4 wherein a porous plug formed from glass wool or steel wool is located at the open end of the chamber.

* * * * *